(12) United States Patent
Podolsky

(10) Patent No.: US 6,316,218 B1
(45) Date of Patent: Nov. 13, 2001

(54) INTESTINAL TREFOIL PROTEINS

(75) Inventor: Daniel K. Podolsky, Wellesley Hills, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/056,868

(22) Filed: Jan. 27, 1998

Related U.S. Application Data

(63) Continuation of application No. 08/191,352, filed on Feb. 2, 1994, now abandoned, which is a continuation of application No. 08/037,741, filed on Mar. 25, 1993, now abandoned, which is a continuation of application No. 07/837,192, filed on Feb. 13, 1992, now abandoned, which is a continuation-in-part of application No. 07/655,965, filed on Feb. 14, 1991, now abandoned.

(51) Int. Cl.$^7$ .......................... C12P 21/06; C12N 15/00; C12N 1/20; C07H 21/04
(52) U.S. Cl. ...................... 435/69.1; 435/70.1; 435/71.1; 435/320.1; 435/325; 435/252.3; 435/254.11; 536/23.5
(58) Field of Search ................................ 536/23.1, 23.5; 435/320.1, 325, 252.3, 254.11, 69.1, 69.3, 69.7, 70.1, 71.1; 530/300

(56) References Cited

FOREIGN PATENT DOCUMENTS

WO 96/06861    3/1996   (WO) .

OTHER PUBLICATIONS

International Search Report for PCT/US92/01200 dated May 11, 1992.

Maniatis, T., et al. 1982, Molecular Cloning, A Laboratory Manual, Cold Spring Harbor Laboratory, Cold Spring Harbor, New York, pp. 224–246, 270–307, 310–352, 404–433.

Jorgensen, K.D., et al., 1982, Pancreatic Spasmolytic Polypeptide (PSP): III. Pharmacology of a new porcine pancreatic polypeptide with spasmolytic and gastric acid secretion inhibitory effects, Reg. Pep. 3:231–243.

Thim, L., et al., 1982, Pancreatic Spasmolytic Polypeptide (PSP): II. Radioimmunological determination of PSP in porcine tissues, plasma and pancreatic juice, Regulatory Peptides, 3: 221–230.

Jorgensen, K.H., et al., 1982, Pancreatic Spasmolytic Polypeptide (PSP): I. Preparation and initial chemical characterization of a new polypeptide from porcine pancreas, Regulatory Peptides, 3:207–219.

Jakowlew, S.B., et al., 1984, Sequence of the pS2 mRNA induced by estrogen in the human breast cancer cell line MCF–7, 12:2861–2878.

Frandsen, E.K., et al., 1986, Receptor binding of pancreatic spasmolytic polypeptide (PSP) in rat intestinal mucosal cell membranes inhibits the adenylate cyclase activity, Regulatory Peptides, 16:291–297.

Rio, M.C., et al., 1988, Breast Cancer–Associated pS2 Protein: Synthesis and Secretion by Normal Stomach Mucosa, Science, 241:705–708.

Podolsky, D.K., et al., 1988, Latent Transformed Growth–inhibiting Factor in Human Malignant Effusions, Cancer Research, 48:418–424.

Hauser et al., "hP1.B, a human P–domain peptide homologous with rat intestinal trefoil factor . . . ", Proceedings of the National Academy of Sciences 90: 6961–6965, 1993.

Sands et al., "The Trefoil Peptide Family," Annual Review of Physiology 58: 253–273. 1996.

Suemori et al., "Identification and Characterization of Rat Intestinal Trefoil Factor: Tissue– and Cell–specific member of the Trefoil Protein Family" Proc. Natl. Acad. Sci. USA 88:11017–11021 (1991).

Primary Examiner—Patricia A. Duffy
(74) Attorney, Agent, or Firm—Clark & Elbing LLP

(57) ABSTRACT

Intestinal trefoil factors and nucleic acids encoding intestinal trefoil factors are disclosed. The intestinal trefoil factors disclosed are resistent to destruction in the digestive tract and can be used for the treatment of peptic ulcer diseases, inflammatory bowel diseases and other insults.

8 Claims, 7 Drawing Sheets

```
gaagtttgcg tgctgcc                                                           17 atg gag acc aga gcc ttc tgg ata acc ctg ctg gtc ctg gtt             62
gct ggg tcc tcc tgc aaa gcc cag gaa ttt gtt ggc cta tct cca        107
agc caa tgt atg gcg cca aca aat gtc agg gtg gac tgt aac tac        152
ccc act gtc aca tca gag cag tgt aac aac cgt ggt tgc tgt ttt        197
gac tcc agc atc cca aat gtg ccc tgg tgc ttc aaa cct ctg caa        242
gag aca gaa tgt aca ttt                                            260 tgaagctgtc caggctccag gaaggagct ccacaccctg gactcttgct               310
gatggtagtg gcccaggta acactcaccc ctgatctgct ccctcgcgcc               360
ggccaatata ggagctggga gtccagaaga ataaagacct tacagtcagc              410
acaaggctgt tctaattgcg g                                             431
```

FIG. 1

Met Glu Thr Arg Ala Phe Trp Ile Thr Leu Leu Val Leu Val
                    5                  10              15
Ala Gly Ser Ser Cys Lys Ala Gln Glu Phe Val Gly Leu Ser Pro
                20                  25                  30
Ser Gln Cys Met Ala Pro Thr Asn Val Arg Val Asp Cys Asn Tyr
                35                  40                  45
Pro Thr Val Thr Ser Glu Gln Cys Asn Asn Arg Gly Cys Cys Phe
                50                  55                  60
Asp Ser Ser Ile Pro Asn Val Pro Trp Cys Phe Lys Pro Leu Gln
                65                  70                  75
Glu Thr Glu Cys Thr Phe
                80

FIG. 2

```
rITF  METRAFWITLLLVLVAGSSCKAQEFVGLSPSQCMAPTNVRVDCNYPTVTSEQCNNRGCC
pS2   ------------------------------EAQ------TETCTVAPRERQNCGFPGVTPSQCANKGCC
PSP   ------------------------EKPAACRCSRQDPKN-RVNCGFPGITSDQCFTSGCC rITF  FDSSIPNVPWCFK-----PLQ-----ETECT-----F
pS2   FDDTVRGVPWCFY-----PNTIDVPPEECE-----F
PSP   FDSQVPGVPWCFK-----PLP-----AQESEECVMEV
```

FIG. 3

```
  1 gatgctggggctggtcctggccttgctgtcctgtctgctgaggagtacgtgtgggcct   60
    -+---------+---------+---------+---------+---------+---------+-
      M  L  G  L  V  L  A  L  L  S  S  S  A  E  E  Y  V  G  L 61 gtctgcaaaccagtgtgccgtgccggccaaggacacaggtgactgcggctaccccatgt  120
    -+---------+---------+---------+---------+---------+---------+-
      S  A  N  Q  C  A  V  P  A  K  D  R  V  D  C  G  Y  P  H  V 121 cacccccaaggagtgcaacaaccggggctgctgctttgactccaggatccctggagtgcc  180
    -+---------+---------+---------+---------+---------+---------+-
      T  P  K  E  C  N  N  R  G  C  C  F  D  S  R  I  P  G  V  P 181 ttggtgtttcaagccccctgcaggaagcagaatgcacctcctgaggcacctccagctgccc  240
    -+---------+---------+---------+---------+---------+---------+-
      W  C  F  K  P  L  Q  E  A  E  C  T  F 241 ctgggatgcaggctgagcaccctgcccggcaagcttcctgattgctgcaggcactgttcatctc  300
    -+---------+---------+---------+---------+---------+---------+-

301 agtttctgtcccttgctcccggcaagcttcctgtgaaagttcatatctggagcctg  360
    -+---------+---------+---------+---------+---------+---------+-

361 atgtcttaacgaataaaggtcccatgctccaccgAAAAA                       400
    -+---------+---------+---------+-----
```

Fig. 6

INTESTINAL TREFOIL PROTEINS

This application is a continuation of U.S. Ser. No. 08/191,352 filed Feb. 2, 1994 now abandoned, which is a continuation of U.S. Ser. No. 08/037,741 filed Mar. 25, 1993 now abandoned, which is a continuation of U.S. Ser. No. 07/837,192 filed Feb. 13, 1992 now abandoned, which is a continuation-in-part of U.S. Ser. No. 07/655,965 filed Feb. 14, 1991 (now abandoned).

BACKGROUND

The field of the invention is peptides useful for treatment of disorders of the digestive system.

Jørgensen et al. (Regulatory Peptides 3:231, 1982) describe a porcine pancreatic peptide, pancreatic spasmolytic peptide (PSP). PSP was found to inhibit "gastrointestinal motility and gastric acid secretion in laboratory animal after parenteral as well as oral administration." It was suggested that "if the results in animal experiments can be confirmed in man, PSP may posses a potential utility in treatment of gastroduodenal ulcer diseases.

SUMMARY OF THE INVENTION

In a first aspect, the invention features a purified nucleic acid encoding an intestinal trefoil factor (ITF).

In preferred embodiments, the intestinal trefoil factor is mammalian intestinal trefoil factor, preferably human, rat, bovine, or porcine intestinal trefoil factor. In another preferred embodiment, the purified nucleic acid encoding an intestinal trefoil factor is present within a vector.

In a related aspect, the invention features a cell that includes a vector encoding an intestinal trefoil factor.

In another related aspect, the invention features a substantially pure intestinal trefoil factor. In a preferred embodiment, the polypeptide is detectably labelled. In a related aspect, the invention features a therapeutic composition that includes an intestinal trefoil factor and a pharmacologically acceptable carrier.

In another aspect, the invention features a monoclonal antibody which preferentially binds (i.e., forms an immune complex with) an intestinal trefoil factor. In a preferred embodiment, the monoclonal antibody is detectably labelled.

In a related aspect, the invention features a method for detecting human intestinal trefoil factor in a human patient. The method includes the steps of contacting a biological sample obtained from the patient with a monoclonal antibody which preferentially binds intestinal trefoil factor, and detecting immune complexes formed with the monoclonal antibody. In preferred embodiments the biological sample is an intestinal mucosal scraping, or serum.

In a related aspect, the invention features a method for treating digestive disorders in a human patient, which method involves administering to the patient a therapeutic composition that includes an intestinal trefoil factor and a pharmacologically acceptable carrier.

In another aspect, the invention features a method for detecting binding sites for intestinal trefoil factor in a patient. The method involves contacting a biological sample obtained from the patient with the factor, and detecting the factor bound to the biological sample as an indication of the presence of the binding sites in the sample. By "binding sites", as used herein, is meant any antibody or receptor that binds to an intestinal trefoil factor protein, factor, or analog. The detection or quantitation of binding sites may be useful in reflecting abnormalities of the gastrointestinal tract.

In another aspect, the invention features substantially pure trefoil factor. In preferred embodiments, the intestinal trefoil factor is human, porcine, or bovine trefoil factor.

The term "intestinal trefoil factor" ("ITF") includes any protein which is substantially homologous to rat intestinal trefoil factor (FIG. 2, SEQ ID NO 2) and which is expressed in the large intestine, small intestine, or colon to a greater extent than it is expressed in tissues other than the small intestine, large intestine, or colon. Also included are: allelic variations; natural mutants; induced mutants; proteins encoded by DNA that hybridizes under high or low stringency conditions to ITF encoding nucleic acids retrieved from naturally occurring material; and polypeptides or proteins retrieved by antisera to ITF, especially by antisera to the active site or binding domain of ITF. The term also includes other chimeric polypeptides that include an ITF.

The term ITF also includes analogs of naturally occurring ITF polypeptides. Analogs can differ from naturally occurring ITF by amino acid sequence differences or by modifications that do not affect sequence, or by both. Analogs of the invention will generally exhibit at least 70%, more preferably 80%, more preferably 90%, and most preferably 95% or even 99%, homology with all or part of a naturally occurring ITF sequence. The length of comparison sequences will generally be at least about 8 amino acid residues, usually at least 20 amino acid residues, more usually at least 24 amino acid residues, typically at least 28 amino acid residues, and preferably more than 35 amino acid residues. Modifications include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes that affect glycosylation derived from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine. Analogs can differ from naturally occuring ITF by alterations of their primary sequence. These include genetic variants, both natural and induced. Induced mutants may be derived by various techniques, including random mutagenesis of the encoding nucleic acids using irradiation or exposure to ethanemethylsulfate (EMS), or may incorporate changes produced by site-specific mutagenesis or other techniques of molecular biology. See, Sambrook, Fritsch and Maniatis (1989), *Molecular Cloning: A Laboratory Manual* (2d ed.), CSH Press, hereby incorporated by reference. Also included are analogs that include residues other than Inaturally occurring L-amino acids, e.g., D-amino acids or non-naturally occurring or synthetic amino acids, e.g., β or γ amino acids.

In addition to substantially full-length polypeptides, the term ITF, as used herein, includes biologically active fragments of the polypeptides. As used herein, the term "fragment", as applied to a polypeptide, will ordinarily be at least about 10 contiguous amino acids, typically at least about 20 contiguous amino acids, more typically at least about 30 contiguous amino acids, usually at least about 40 contiguous amino acids, preferably at least about 50 contiguous amino acids, and most preferably at least about 60 to 80 or more contiguous amino acids in length. Fragments of ITF can be generated by methods known to those skilled in the art. The ability of a candidate fragment to exhibit a biological activity of ITF can be assessed by methods known to those skilled in the art. Also included in the term are biologically active ITF polypeptides containing amino acids that are normally removed during protein processing, including additional amino acids that are not required for the biological activity of the polypeptide, or including additional amino acids that result from alternative mRNA splicing or alternative protein processing events.

An ITF polypeptide, fragment, or analog is biologically active if it exhibits a biological activity of a naturally occurring ITF, e.g., the ability to alter gastrointestinal motility in a mammal.

The invention also includes nucleic acid sequences, and purified preparations thereof, that encode the ITF polypeptides described herein. The invention also includes antibodies, preferably monoclonal antibodies, that bind specifically to ITF polypeptides.

As used herein, the term "substantially pure" describes a compound, e.g., a nucleic acid, a protein, or a polypeptide, e.g., an ITF protein or polypeptide, that is substantially free from the components that naturally accompany it. Typically, a compound is substantially pure when at least 60%, more preferably at least 75%, more preferably at least 90%, and most preferably at least 99%, of the total material (by volume, by wet or dry weight, or by mole per cent or mole fraction) in a sample is the compound of interest. Purity can be measured by any appropriate method, e.g., in the case of polypeptides by column chromatography, polyacrylamide gel electrophoresis, or HPLC analysis.

By "isolated DNA" is meant that the given DNA is free of the genes which, in the naturally-occurring genome of the organism from which the given DNA of the invention is derived, flank the given DNA. The term "isolated DNA" thus encompasses, for example, cDNA, cloned genomic DNA, and synthetic DNA. A "purified nucleic acid", as used herein, refers to a nucleic acid sequence that is substantially free of other macromolecules (e.g., other nucleic acids and proteins) with which it naturally occurs within a cell. In preferred embodiments, less than 40% (and more preferably less than 25%) of the purified nucleic acid preparation consists of such other macromolecules.

"Homologous", as used herein, refers to the subunit asequence similarity between two polymeric molecules, e.g., between two nucleic acid molecules, e.g., two DNA molecules, or two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half, e.g., 5 of 10, of the positions in two compound sequences are homologous then the two sequences are 50% homologous, if 90% of the positions, e.g., 9 of 10, are matched or homologous the two sequences share 90% homology. By way of example, the DNA sequences 3'ATTGCC'5 and 3'TATGGC'5 share 50% homology. By "substantially homologous" is meant largely but not wholly homologous.

The ITF proteins of the invention are resistent to destruction in the digestive tract, and can be used for treatment of peptic ulcer diseases, inflammatory bowel diseases, and for protection of the intestinal tract from injury caused by bacterial infection, radiation injury or other insults. An ITF protein, fragment, or analog can also be used to treat neoplastic cancer.

Other features and advantages of the invention will be apparent from the following description of the preferred embodiments thereof, and from the claims.

DETAILED DESCRIPTION

The drawings will first be briefly described.

Drawings

FIG. 1 is a depiction of the nucleotide sequence of rat trefoil factor (SEQ ID NO: 1).

FIG. 2 is a depiction of the deduced amino acid sequence of rat trefoil factor (SEQ ID NO: 2).

FIG. 3 is a depiction of the amino acid sequences of rat trefoil factor (SEQ ID NO: 10) pS2 protein (SEQ ID NO: 11) and pancreatic spasmolytic polypeptide (SEQ ID NO: 12). The sequences are aligned so as to illustrate the amino acid sequence homology between the proteins. Dashes (-) indicate the insertion of spaces which improve alignment. Bars ( ) indicate sequence identities.

Figure 4A:
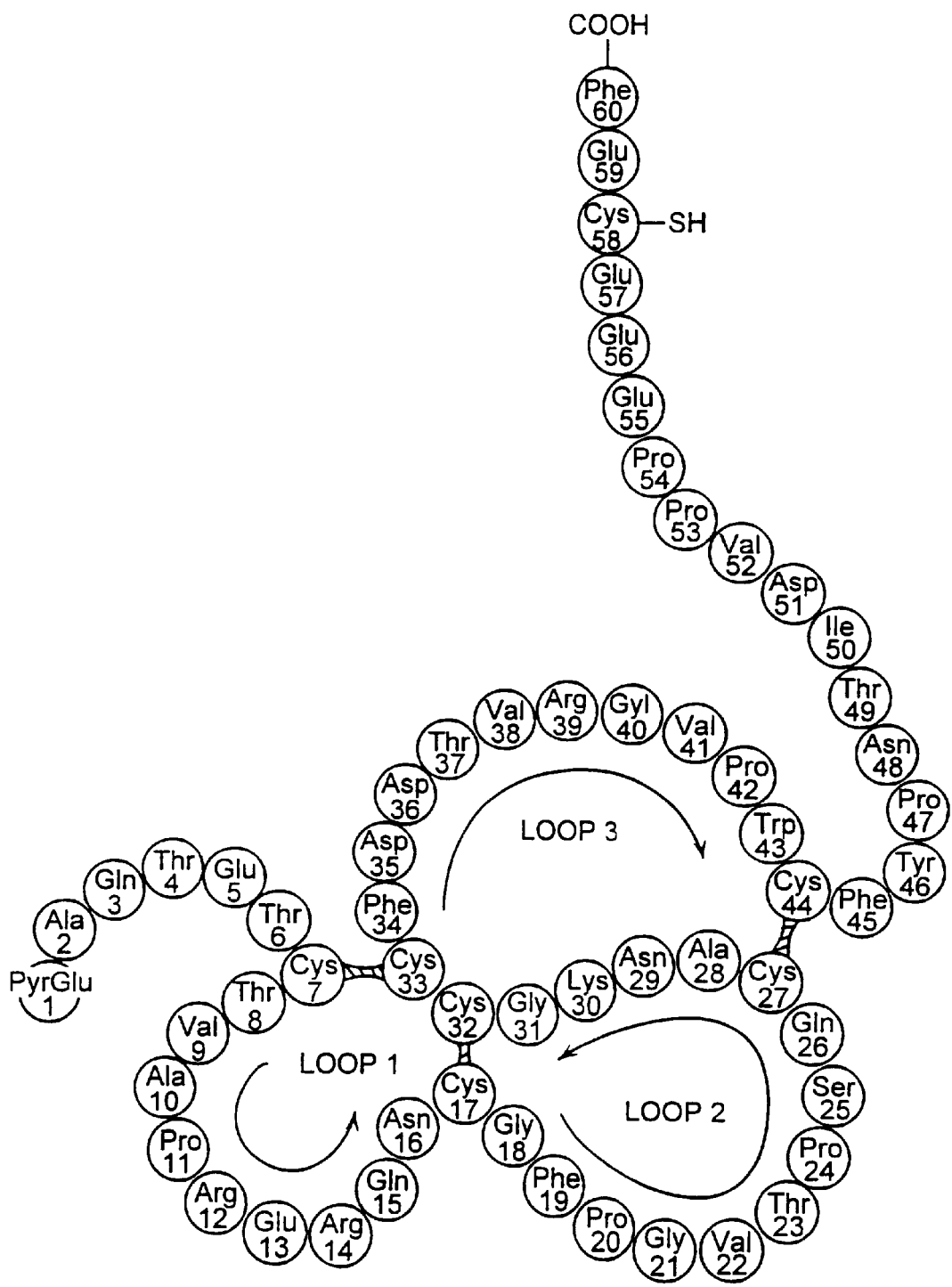
Figure 5:
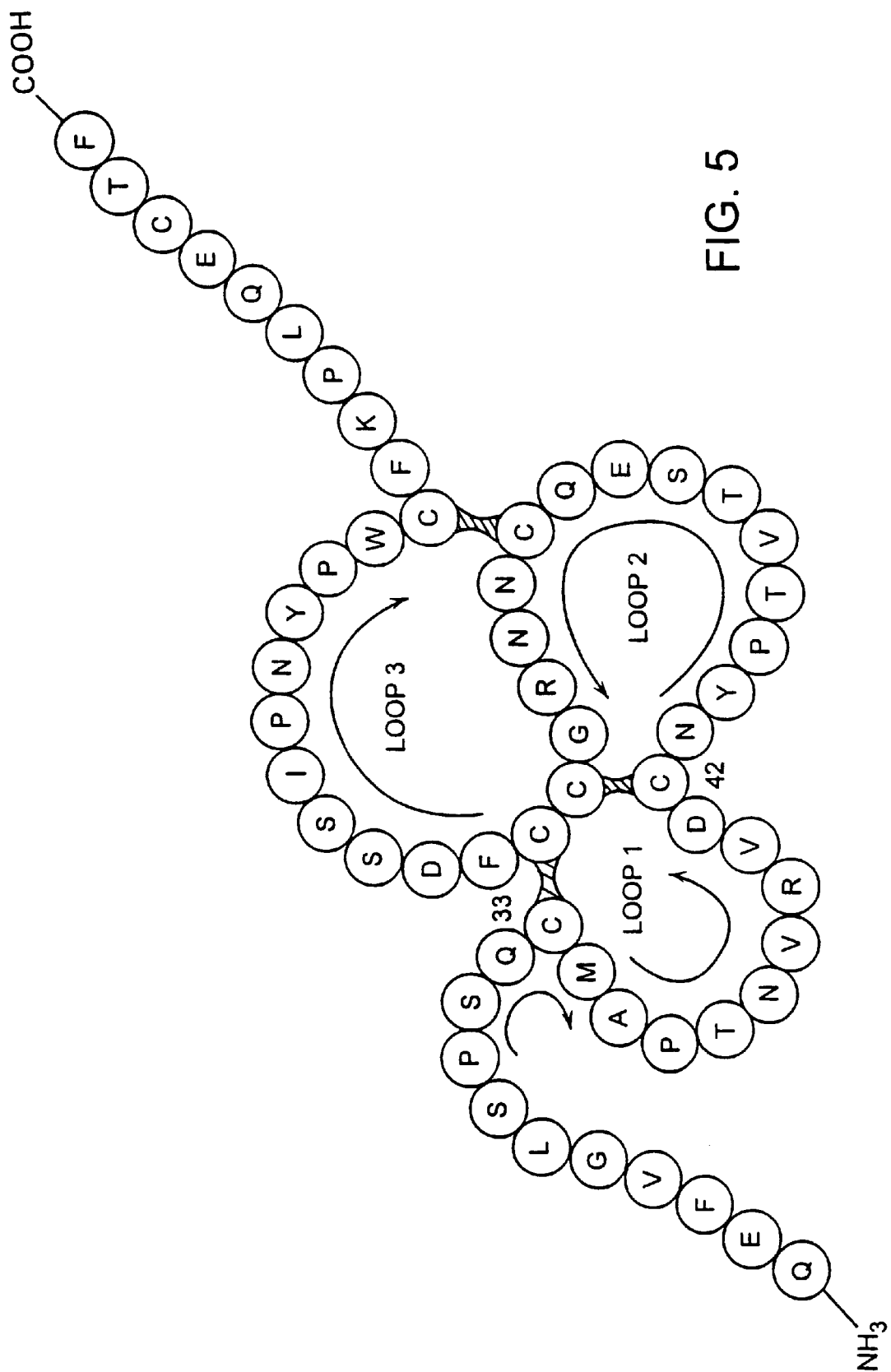

FIG. 4 depicts the disulfide bond structure proposed for pS2 (panel A) and PSP (panel B; SEQ ID NO: 15);

FIG. 5 is a depiction of the proposed disulfide bond structure of rat intestinal trefoil factor (SEQ ID NO: 16).

FIG. 6 is a depiction of the nucleotide sequence (SEQ ID NO: 3) of the human intestinal trefoil factor cDNA and the corresponding deduced amino acid sequence (SEQ ID NO: 4).

Purification and Cloning of rITF

An inhibitor of soft agar colony formation by human breast carcinoma-derived BT-20 cells (ATTC HTB79) was isolated from cytology-positive human malignant effusions (Podolsky et al., *Cancer Res.* 48:418, 1988; hereby incorporated by reference). The factor also inhibited soft agar colony formation by human colon carcinoma-derived HCT-15 cells (ATTC-CCL225). Inhibition was not observed for polyoma and murine sarcoma virus transformed rodent fibroblast lines. The isolated factor (transformed cell-growth inhibiting factor or TGIF) had an apparent molecular weight of 110,000 kD and appeared to consist of two 55,000 kD subunits linked by sulfhydryl bonds.

The purified protein was partially sequenced. The sequence from the amino terminal 14 amino acids was used to produce a set of degenerate oligonucleotide probes for screening of a rat intestinal epithelial cell cDNA library.

A rat intestinal cDNA library (Lambda ZAP° II, Stratagene, La Jolla, Calif.) was produced by standard techniques (Ausubel et al., eds., *Current Protocols in Molecular Biology,* John Wiley & Sons, New York, 1989) using cells purified by the method of Weisner (*J. Biol Chem.* 248:2536, 1973). Screening of the cDNA library with the fully degenerate oligonucleotide probe described above resulted in the selection of 21 clones. One of the clones (T3411) included a core sequence which encoded a single open reading frame. The nucleotide sequence of the open reading frame and flanking DNA is presented in FIG. 1 (SEQ ID NO 1). The insert present in T3411 was nick translated (Ausubel et al., supra) to produce a radioactively labelled probe for Northern blot analysis of rat poly(A)$^+$ RNA. Northern analysis demonstrated that RNA corresponding to the cloned cDNA fragment was expressed in small intestine, large intestine, and kidney; no expression was detected in the lung, spleen, heart, testes, muscle, stomach, pancreas, or liver. In the tissues in which the RNA was expressed, the level was comparable to that of actin.

Figure 4B:
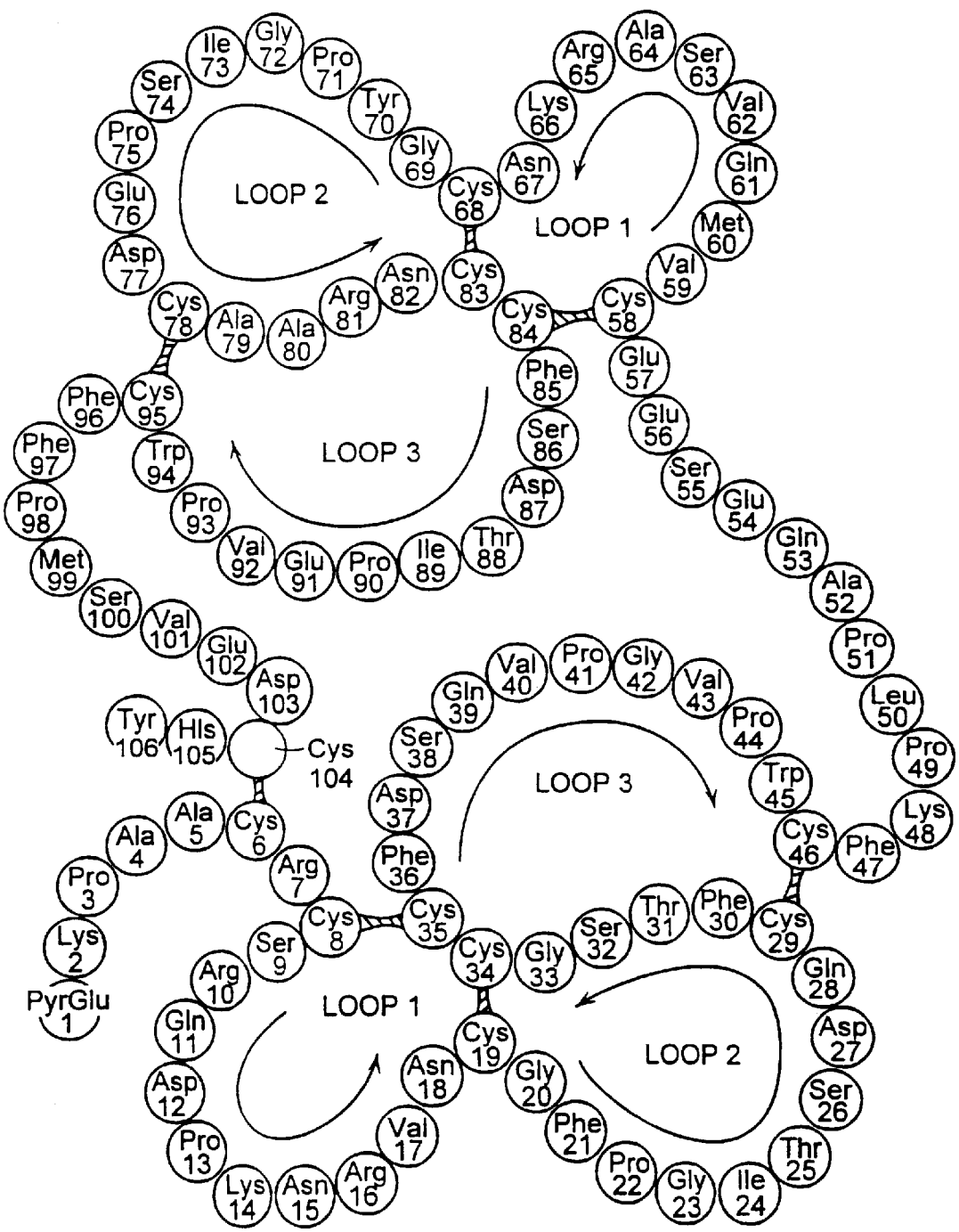

The open reading frame of clone T3411 encoded an 81 amino acid peptide (FIG. 2; SEQ ID NO 2). Comparison of the sequence of the encoded peptide, referred to as rat intestinal trefoil factor (rITF), to the sequence of proteins in the Genebank database revealed significant homology to human breast cancer associated peptide (pS2; Jakowlev et al., *Nucleic Acids Res.* 12:2861, 1984) and porcine pancreatic spasmolytic peptide (PSP; Thim et al., *Biochem. Bio-* phys. Acta 827:410, 1985). FIG. 3 illustrates the homology between rITF, PSP and pS2. Porcine pancreatic spasmolytic factor (PSP) and pS2 are both thought to fold into a characteristic structure referred to as a trefoil. A trefoil structure consists of three loops formed by three disulfide bonds. pS2 is thought to include one trefoil (FIG. 4A), and PSP is thought to include two trefoils (FIG. 4B). The region of rITF (nucleotide 114 to nucleotide 230 which encodes cys to phe) which is most similar to PSP and pS2 includes six cysteines all of which are in the same position as the cysteines which make up the trefoil in pS2 (FIG. 3). Five of these six cysteines are in the same position as the cysteines which form the amino terminal trefoil of PSP (FIG. 3). FIG. 5 depicts the proposed disulfide bond configuration of rITF.

Based on homology to PSP and pS2 (Mori et al., *Biochem. Biophys. Res. Comm.* 155:366, 1988; Jakowlew et al., *Nucleic Acids Res.* 12:2861, 1984), rITF includes a presumptive pro- sequence (met$^1$ to ala$^{22}$) in which 12 of 22 amino acids have hydrophobic side chains.

Production of Anti-rITF Antibodies

A peptide corresponding to the carboxy-terminal 21 amino acids of rITF was synthesized and coupled to bovine serum albumin (BSA). This conjugate (and the unconjugated peptide) was used to raise polyclonal antibodies in rabbits. All procedures were standard protocols such as those described in Ausubel et al. (supra). The anti-rITF antibodies were used in an indirect immunoflouresce assay for visualization of rITF in rat tissues. Cryosections of rat tissues were prepared using standard techniques, and fluorescein labelled goat anti-rabbit monoclonal antibody (labelled antibodies are available from such suppliers Kirkegaard and Perry Laboratories, Gaithersberg, Md.; and Bioproducts for Science, In., Indianapolis, Ind.) was used to detect binding of rabbit anti-rITF antibodies. By this analysis rITF appears to be present in the globlet cells of the small intestine but not in the stomach or the pancreas.

Cloning of Human Intestinal Trefoil Factor

DNA encoding the rat intestinal trefoil factor can be used to identify a cDNA clone encoding the human intestinal trefoil factor (hITF). This can be accomplished by screening a human colon cDNA library with a probe derived from rITF or with a probe derived from part of the hITF gene. The latter probe can be obtained from a human colon or intestinal cDNA using the polymerase chain reaction to isolate a part of the hITF gene. This probe can then serve as a specific probe for the identification of clones encoding all of the hITF gene.

Construction of a cDNA Library

A human colon or intestinal cDNA library in λgt10 or λgt11, or some other suitable vector is useful for isolation of hITF. Such libraries may be purchased (Clontech Laboratories, Palo Alto, Calif.: HLI034a, HLI0346b). Alternatively, a library can be produced using mucosal scrapings from human colon or intestine. Briefly, total RNA is isolated from the tissue essentially as described by Chirgwin et al. (*Biochemistry* 18:5294, 1979; see also Ausubel et al., supra). An oligo (dT) column is then used to isolate poly(A)$^+$ RNA by the method of Aviv et al. (*J. Mol. Biol.* 134:743, 1972; see also Ausubel et al., supra). Double-stranded cDNA is then produced by reverse transcription using oligo (dT)$_{12-18}$ or random hexamer primers (or both). RNAse H and *E. coli* DNA poli are then used to replace the RNA strand with a second DNA strand. In a subsequent step *E. coli* DNA ligase and T4 DNA polymerase are used to close gaps in the second DNA strand and create blunt ends. Generally, the cDNA created is next methylated with EcoRI methylase and EcoRI linkers are added (other linkers can be used depending on the vector to be used). In subsequent steps the excess linkers are removed by restriction digestion and the cDNA fragments are inserted into the desired vector. See Ausubel et al., supra and Sambrook et al. (*Molecular Cloning: A Laboratory Manual,* Cold Spring Harbor Laboratory, Cold Spring Harbor, N.Y., 1990) for detailed protocols. Useful vectors include: λgt11, λgt10, Lambda ZAP® II vector, Lambda Uni-ZAP™ XR vector, all available from Stratagene (La Jolla, Calif.).

The cDNA library must be packaged into phage; this is most readily accomplished by use of a commercial in vitro packaging kit, e.g., Gigapack® II Gold or Gigapack® II Plus (Stratagene, La Jolla, Calif.). See Ausubel et al. (supra) for packaging protocols and suitable host strains. The library is preferably amplified soon after packaging; this step generates sufficient clones for multiple screening of the library. See Ausubel et al. supra or Sambrook et al. supra for details of amplification protocols and procedures for storing the amplified library.

Screening of the cDNA Library

To screen the library it must be placed on an appropriate host strain (e.g., Y1090 or Y1088 for λgt10 libraries, C600hflA for λgt10 libraries). After plating the phage, plaques are transferred to nitrocellulose or nylon filters (See Ausubel et al., supra and Sambrook et al. supra). The filters are then probed with α$^{32}$P-labelled nick translated probe derived from rITF. The probe is preferentially generated using a portion of the region of rITF DNA coding for the trefoil structure (nucleotides 114 to 230 of SEQ ID NO. 1 which encode cyS32 to phe$^{71}$ of SEQ ID NO. 2). This region is conserved between rITF, pS2 and PSP, and it is likely that this region is conserved between rITF and hITF. Once a plaque is identified several cycles of plaque purification are required to isolate a pure clone encoding hITF. A phage DNA isolation is performed and the cDNA insert can be subdloned into an appropriate vector for restriction mapping and sequencing. If the phage vector is Lambda ZAP® II, coinfection with helper phage allows rescue and recircularization of pBluescript SK$^-$ phagemid vector (Stratagene, La Jolla, Calif.) harboring the cDNA; alternatively the phage clone is purified and the cDNA insert is subcloned into a vector suitable for restriction mapping and sequencing. If the clone does not contain the entire hITF gene (as assessed by homology to rITF and the presence of start and stop codons), the library can be rescreened with the original rITF probe or, preferably, with a probe generated from the hITF clone obtained. If none of the clones contain the intact gene, it can be reconstructed from clones which bear overlapping fragments of hITF.

Direct Isolation of an hITF Probe by PCR

It is possible to isolate part of the hITF gene directly from the packaged library or cDNA. To isolate a portion of hITF directly from the packaged library, a pair of oligonucleotide primers and Taq polymerase are used to amplify the DNA corresponding to the hITF gene. The primers used would be approximately 15–20 nucleotides long and correspond in sequence to the 5'-most and 3'-most portions of the rITF coding sequence. Friedman et al. (in *PCR Protocols: A Guide to Methods and Applications,* Innis et al., eds., Academic Press, San Diego) describe a procedure for such amplification. Briefly, phage particles are disrupted by heating; Taq polymerase, primers (300 pmol of each), dNTPs, and Taq polymerase buffer are added; and the mixture is thermally cycled to amplify DNA. The amplified DNA is isolated by agarose gel electrophoresis. The ends of the fragment are prepared for ligation into an appropriate vector by making them flush with T4 polymerase and, if desired, adding linkers. Alternatively, a restriction site may be engineered into the fragment by using primers which have sequence added to their 5' ends which sequence will generate an appropriate sticky end when digested. For example the sequence: 5'-GGGCGGCCGC-3' (SEQ ID NO: 5) can be added to the 5' end of each primer. This sequence includes the NotI restriction site flanked at the 5' end by the sequence: GG. The additional nucleotides prevent the 5' ends from denaturing and interfering with subsequent restriction digestion with NotI. The gel purified DNA of the appropriate size is next cloned into a cloning vector for sequencing and restriction mapping. This clone will not have the entire hITF sequence, rather it will be a combination of hITF (the region between the sequences corresponding to the primers) and rITF (the 5' and 3' ends which correspond to the primer sequences). However, this DNA can be used to generate a labelled probe (produced by nick translation or random primer labelling) which, since it is the correct hITF sequence, can be used in a high stringency screening of the library from which the cDNA was originally isolated. In an alternative approach, cDNA can be used in the above procedure instead of a packaged library. This eliminates the steps of modifying the cDNA for insertion into a vector as well as cDNA packaging and library amplification. Ausubel et al. supra provides a protocol for amplification of a particular DNA fragment directly from cDNA and a protocol for amplification from poly(A)$^+$ RNA.

Identification of a Presumptive Human ITF Clone

A nick translated probe derived from rITF cDNA (corresponding to nucleotides 1 to 431 of SEQ ID No. 1) was used for Northern blot analysis of poly(A)$^+$ RNA derived from human intestinal mucosal scrapings. Probe hybridization and blot washing were carried out according to standard procedures. Probe ($5 \times 10^5$ cpm/ml hybridization buffer) was hybridized to the filter at 45° C. in 5×SSC with 30% formamide. The filter was then washed at 60° C. in 5×SSC with 40% formamide. Using this protocol a band was clearly visible after an overnight exposure of the filter with an intensifying screen. This result indicated that there is sufficient homology between rITF and hITF to allow the use of probes derived from the sequence of the rITF gene for identification of the hITF gene.

A human intestinal cDNA library was obtained from Clontech (Palo Alto, Calif.). Alternatively, a human intestinal cDNA library may be produced from mucosal scrapings as described above. Four oligonucleotide probes were selected for screening the library cDNA. Two of the probes correspond to sequences within the region of rITF encoding the trefoil and are referred to as internal probes (5'-gtacattctgtctcttgcaga-3' (SEQ. ID. NO.6) and 5'-taaccctgctgctgctggtcctgg-3' (SEQ ID NO: 7). The other two probes recognize sequences within rITF but outside of the trefoil encoding region and are referred to as external probes (5'-gtttgcgtgctgccatggaga-3' (SEQ ID NO: 8) and 5'-ccgcaattagaacagccttgt-3' (SEQ ID NO: 9)). These probes were tested for their utility by using them to screen the rat intestinal cDNA library described above. Each of the four probes could be used to identify a clone harboring all or part of the rITF gene. This result indicates that these probes may be used to screen the human intestinal library for the presence of hITF.

The internal probes were used as described above to amplify a DNA fragment from human colon library cDNA (Clontech, Palo Alto, Calif.). Linkers were added to the isolated DNA fragment which was then inserted into pBluescript phagemid vector (Stratagene, La Jolla, Calif.). The region of this clone corresponding to the sequence of human cDNA (i.e., not including the sequence corresponding to the internal probes) was used to make a radioactively labelled probe by random oligonucleotide-primed synthesis (Ausebel et al., supra). This probe was then used to screen the human colon cDNA library. This screening led to the identification of 29 clones. One of these clones (HuPCR-ITF) was nick-translated to generate a probe for Northern analysis of poly(A)$^+$ RNA isolated from human intestinal mucosal scrapings. A single band of roughly the same size as the rat transcript (approximately 0.45 kD) was observed.

Northern analysis of poly(A)$^+$ isolated from human tissues indicated that RNA corresponding to this probe was expressed in the small intestine and the large intestine but not in the stomach or the liver. These results indicate that the clone does not encode the human homolog of porcine PSP. Porcine PSP is expressed in porcine pancreas and is not significantly expressed in the small or large intestine. These results also distinguish the cloned gene from pS2 which is expressed in the stomach.

FIG. 6 shows the nucleic acid sequence information for human ITF cDNA (SEQ ID NO: 4), along with the deduced amino acid sequence in one-letter code (SEQ ID NO: 4). This clone was obtained by the methods described above.

Production of hITF

The isolated hITF gene can be cloned into a mammalian expression vector for protein expression. Appropriate vectors include pMAMneo (Clontech, Palo Alto, Calif.) which provides a RSV-LTR enhancer linked to a dexamethasone-inducible MMTV-LTR promoter, an SV40 origin of replication (allows replication in COS cells), a neomycin gene, and SV40 splicing and polyadenylation sites. This vector can be used to express the protein in COS cells, CHO cells, or mouse fibroblasts. The gene may also be cloned into a vector for expression in drosophila cells using the baculovirus expression system.

Purification of Intestinal Trefoil Factor

Intestinal trefoil factor can be purified from intestinal mucosal scrapings of human, rats or any other ispecies which expresses ITF (pigs and cows may provide a source of ITF). The purification procedure used for PSP will be useful for the purification of ITF since the proteins are likely to be homologous. Jorgensen et al. describes a method for purification of PSP (Regulatory Peptides 3:207, 1982). The preferred method is the second approach described by Jorgensen et al. (supra). This method involves chromatography of SP-Sephadex C-25 and QAE Sephadex A-25 columns (Sigma, St. Louis, Mo.) in acidic buffer.

Anti-Intestinal Trefoil Factor Monoclonal Antibodies

Anti-intestinal trefoil factor monoclonal antibodies can be raised against synthetic peptides whose sequences are based on the deduced amino acid sequence of cloned hITF (SEQ ID NO: 4). Most commonly the peptide is based on the amino- or carboxy-terminal 10–20 amino acids of the protein of interest (here hITF). The peptide is usually chemically cross-linked to a carrier molecule such as bovine serum albumin or keyhole limpet hemocyanin. The peptide is selected with the goal of generating antibodies which will cross-react with the native hITF. Accordingly, the peptide should correspond to an antigenic region of the peptide of interest. This is accomplished by choosing a region of the protein which is (1) surface exposed, e.g., a hydrophobic region or (2) relatively flexible, e.g., a loop region or a β-turn region. In any case, if the peptide is to be coupled to a carrier,it must have an amino acid with a side chain capable of participating in the coupling reaction. See Hopp et al. (*Mol. Immunol.* 20:483, 1983; *J. Mol. Biol.* 157:105, 1982) for a discussion of the issues involved in the selection of antigenic peptides. A second consideration is the presence of a protein homologous to hITF in the animal to be immunized. If such a protein exists, it is important to select a region of hITF which is not highly homologous to that homolog.

For hITF, peptides that correspond to the amino-terminal or carboxy-terminal 15 amino acids are likely to be less homologous across species and exposed to the surface (and thus antigenic). Thus they are preferred for the production of monoclonal antibodies. Purified hITF can also be used for the generation of antibodies.

Use

In the practice of the present invention ITF may be administered orally, intravenously, or intraperitoneally for treatment of peptic ulcer diseases, inflammatory bowel diseases, and for protection of the intestinal tract from injury caused by bacterial infection, radiation injury or other insults. The mode of administration, dosage, and formulation of ITF depends upon the condition being treated.

Other Embodiments

Other embodiments are within the following claims. For example, ITF may be used to produce monoclonal antibodies for the detection of ITF in intestinal tissue or blood serum by means of an indirect immunoassay. ITF may be detectably labelled and used in an in situ hybridization assay for the detection of ITF binding sites. Labels may include, but are not limited to, florescein or a radioactive ligand.

ITF may be used to protect and stabilize other proteins. This protection is accomplished by forming a hybrid molecule in which all or part of ITF is fused to either the carboxy-terminus or the amino-terminus (or both) of the protein of interest. Because ITF is resistant to degradation in the digestive system, it will protect the protein of interest from such degradation. As a consequence, the protein of interest is likely to remain active in the digestive system and/or will be more readily absorbed in an intact form.

DEPOSIT STATEMENT

The human intestinal trefoil clone described herein has been deposited under conditions in which access will be available during the pendency of the present patent application to those determined by the Commissioner of Patents and Trademarks to be entitled thereto under 37 C.F.R. §1.14 and 35 U.S.C. §122. More specifically, the human intestinal trefoil clone described herein has been deposited with the American Type Culture Collection (Manassas, Va.) and assigned Accession Number 98767.

What is claimed is:

1. An isolated nucleic acid that encodes an intestinal trefoil factor (ITF) polypeptide, the polypeptide having the sequence of the polypeptide encoded by the cDNA clone deposited with the American Type Culture Collection and assigned Accession Number 98767.

2. A vector comprising the isolated nucleic acid of claim 1.

3. A cell comprising the vector of claim 2.

4. An isolated nucleic acid that encodes an intestinal trefoil factor (ITF) polypeptide, the nucleic acid comprising the sequence of the cDNA clone deposited with the American Type Culture Collection and assigned Accession Number 98767.

5. An isolated nucleic acid that encodes an intestinal trefoil factor (ITF) polypeptide, the polypeptide comprising the amino acid sequence shown in FIG. 2 (SEQ ID NO:2).

6. A vector comprising the isolated nucleic acid of claim 5.

7. A cell comprising the vector of claim 6.

8. A method for producing an ITF polypeptide by culturing the cell of claim 3 under conditions in which the nucleic acid molecule encoding ITF is expressed.

* * * * *

UNITED STATES PATENT AND TRADEMARK OFFICE
CERTIFICATE OF CORRECTION

PATENT NO. : 6,316,218 B1  Page 1 of 1
DATED : November 13, 2001
INVENTOR(S) : Daniel K. Podolsky It is certified that error appears in the above-identified patent and that said Letters Patent is hereby corrected as shown below:

Column 2,
Line 51, change "Inaturally" to -- naturally --;

Column 3,
Line 42, change "asequence" to -- sequence --;

Column 5,
Line 33, change "In." to -- Inc. --;
Line 62, change "polI" to -- polI --;

Column 6,
Line 36, change "subdloned" to -- subcloned --;

Column 8,
Line 21, change "NO: 4" to -- NO: 3 --;
Line 38, change "ispecies" to -- species --;

Signed and Sealed this

Third Day of September, 2002

Attest:

JAMES E. ROGAN
Attesting Officer  Director of the United States Patent and Trademark Office

SEQUENCE LISTING

```
<160> NUMBER OF SEQ ID NOS: 16

<210> SEQ ID NO 1
<211> LENGTH: 431
<212> TYPE: DNA
<213> ORGANISM: Rattus ITF
<220> FEATURE:
<221> NAME/KEY: CDS
<222> LOCATION: (18)...(260)

<400> SEQUENCE: 1
gaagtttgcg tgctgcc atg gag acc aga gcc ttc tgg ata acc ctg ctg        50
                   Met Glu Thr Arg Ala Phe Trp Ile Thr Leu Leu
                    1               5                  10 ctg gtc ctg gtt gct ggg tcc tcc tgc aaa gcc cag gaa ttt gtt ggc        98
Leu Val Leu Val Ala Gly Ser Ser Cys Lys Ala Gln Glu Phe Val Gly
             15                  20                  25 cta tct cca agc caa tgt atg gcg cca aca aat gtc agg gtg gac tgt       146
Leu Ser Pro Ser Gln Cys Met Ala Pro Thr Asn Val Arg Val Asp Cys
         30                  35                  40 aac tac ccc act gtc aca tca gag cag tgt aac aac cgt ggt tgc tgt       194
Asn Tyr Pro Thr Val Thr Ser Glu Gln Cys Asn Asn Arg Gly Cys Cys
     45                  50                  55 ttt gac tcc agc atc cca aat gtg ccc tgg tgc ttc aaa cct ctg caa       242
Phe Asp Ser Ser Ile Pro Asn Val Pro Trp Cys Phe Lys Pro Leu Gln
 60                  65                  70                  75 gag aca gaa tgt aca ttt tgaagctgtc caggctccag gaagggagct              290
Glu Thr Glu Cys Thr Phe
                 80 ccacaccctg gactcttgct gatggtagtg gcccagggta acactcaccc ctgatctgct    350 ccctcgcgcc ggccaatata ggagctggga gtccagaaga ataaagacct tacagtcagc    410 acaaggctgt tctaattgcg g                                               431
```

```
<210> SEQ ID NO 2
<211> LENGTH: 81
<212> TYPE: PRT
<213> ORGANISM: Rattus ITF

<400> SEQUENCE: 2

Met Glu Thr Arg Ala Phe Trp Ile Thr Leu Leu Val Leu Val Ala
 1               5                  10                  15

Gly Ser Ser Cys Lys Ala Gln Glu Phe Val Gly Leu Ser Pro Ser Gln
                20                  25                  30

Cys Met Ala Pro Thr Asn Val Arg Val Asp Cys Asn Tyr Pro Thr Val
             35                  40                  45

Thr Ser Glu Gln Cys Asn Asn Arg Gly Cys Cys Phe Asp Ser Ser Ile
         50                  55                  60

Pro Asn Val Pro Trp Cys Phe Lys Pro Leu Gln Glu Thr Glu Cys Thr
65                  70                  75                  80

Phe

<210> SEQ ID NO 3
<211> LENGTH: 400
<212> TYPE: DNA
<213> ORGANISM: Homo sapiens
<220> FEATURE:
<221> NAME/KEY: CDS
<222> LOCATION: (2)...(220)

<400> SEQUENCE: 3 g atg ctg ggg ctg gtc ctg gcc ttg ctg tcc tcc agc tct gct gag gag      49
  Met Leu Gly Leu Val Leu Ala Leu Leu Ser Ser Ser Ser Ala Glu Glu
   1               5                  10                  15 tac gtg ggc ctg tct gca aac cag tgt gcc gtg ccg gcc aag gac agg        97
Tyr Val Gly Leu Ser Ala Asn Gln Cys Ala Val Pro Ala Lys Asp Arg
                20                  25                  30 gtg gac tgc ggc tac ccc cat gtc acc ccc aag gag tgc aac aac cgg       145
Val Asp Cys Gly Tyr Pro His Val Thr Pro Lys Glu Cys Asn Asn Arg
             35                  40                  45 ggc tgc tgc ttt gac tcc agg atc cct gga gtg cct tgg tgt ttc aag       193
Gly Cys Cys Phe Asp Ser Arg Ile Pro Gly Val Pro Trp Cys Phe Lys
         50                  55                  60 ccc ctg cag gaa gca gaa tgc acc ttc tgaggcacct ccagctgccc             240
Pro Leu Gln Glu Ala Glu Cys Thr Phe
 65                  70 ctgggatgca ggctgagcac ccttgcccgg ctgtgattgc tgccaggcac tgttcatctc     300 agttttctg tcccttgct cccggcaagc tttctgctga agttcatat ctggagcctg        360 atgtcttaac gaataaaggt cccatgctcc acccgaaaaa                           400

<210> SEQ ID NO 4
<211> LENGTH: 73
<212> TYPE: PRT
<213> ORGANISM: Homo sapiens

<400> SEQUENCE: 4

Met Leu Gly Leu Val Leu Ala Leu Leu Ser Ser Ser Ser Ala Glu Glu
 1               5                  10                  15

Tyr Val Gly Leu Ser Ala Asn Gln Cys Ala Val Pro Ala Lys Asp Arg
                20                  25                  30

Val Asp Cys Gly Tyr Pro His Val Thr Pro Lys Glu Cys Asn Asn Arg
             35                  40                  45
```

Gly Cys Cys Phe Asp Ser Arg Ile Pro Gly Val Pro Trp Cys Phe Lys
    50                  55                  60
Pro Leu Gln Glu Ala Glu Cys Thr Phe
65                  70

<210> SEQ ID NO 5
<211> LENGTH: 10
<212> TYPE: DNA
<213> ORGANISM: Artificial Sequence
<220> FEATURE:
<223> OTHER INFORMATION: synthetically generated primer

<400> SEQUENCE: 5
gggcggccgc                                                          10

<210> SEQ ID NO 6
<211> LENGTH: 21
<212> TYPE: DNA
<213> ORGANISM: Artificial Sequence
<220> FEATURE:
<223> OTHER INFORMATION: synthetically generated primer

<400> SEQUENCE: 6
gtacattctg tctcttgcag a                                             21

<210> SEQ ID NO 7
<211> LENGTH: 24
<212> TYPE: DNA
<213> ORGANISM: Artificial Sequence
<220> FEATURE:
<223> OTHER INFORMATION: synthetically generated primer

<400> SEQUENCE: 7
taaccctgct gctgctggtc ctgg                                          24

<210> SEQ ID NO 8
<211> LENGTH: 21
<212> TYPE: DNA
<213> ORGANISM: Artificial Sequence
<220> FEATURE:
<223> OTHER INFORMATION: synthetically generated primer

<400> SEQUENCE: 8
gtttgcgtgc tgccatggag a                                             21

<210> SEQ ID NO 9
<211> LENGTH: 21
<212> TYPE: DNA
<213> ORGANISM: Artificial Sequence
<220> FEATURE:
<223> OTHER INFORMATION: synthetically generated primer

<400> SEQUENCE: 9
ccgcaattag aacagccttg t                                             21

<210> SEQ ID NO 10
<211> LENGTH: 60
<212> TYPE: PRT
<213> ORGANISM: Artificial Sequence
<220> FEATURE:
<223> OTHER INFORMATION: synthetically generated peptide

<400> SEQUENCE: 10

Glu Ala Gln Thr Glu Thr Cys Thr Val Ala Pro Arg Glu Arg Gln Asn
1               5                   10                  15

```
Cys Gly Phe Pro Gly Val Thr Pro Ser Gln Cys Ala Asn Lys Gly Cys
            20                  25                  30

Cys Phe Asp Asp Thr Val Arg Gly Val Pro Trp Cys Phe Tyr Pro Asn
            35                  40                  45

Thr Ile Asp Val Pro Pro Glu Glu Cys Glu Phe
        50                  55                  60
```

<210> SEQ ID NO 11
<211> LENGTH: 62
<212> TYPE: PRT
<213> ORGANISM: Artificial Sequence
<220> FEATURE:
<223> OTHER INFORMATION: synthetically generated peptide

<400> SEQUENCE: 11

```
Glu Lys Pro Ala Ala Cys Arg Cys Ser Arg Gln Asp Pro Lys Asn Arg
  1               5                  10                  15

Val Asn Cys Gly Phe Pro Gly Ile Thr Ser Asp Gln Cys Phe Thr Ser
            20                  25                  30

Gly Cys Cys Phe Asp Ser Gln Val Pro Gly Val Pro Trp Cys Phe Lys
            35                  40                  45

Pro Leu Pro Ala Gln Glu Ser Glu Glu Cys Val Met Glu Val
        50                  55                  60
```

<210> SEQ ID NO 12
<211> LENGTH: 6
<212> TYPE: DNA
<213> ORGANISM: Artificial Sequence
<220> FEATURE:
<223> OTHER INFORMATION: synthetically generated primer

<400> SEQUENCE: 12 attgcc                                                                  6

<210> SEQ ID NO 13
<211> LENGTH: 6
<212> TYPE: DNA
<213> ORGANISM: Artificial Sequence
<220> FEATURE:
<223> OTHER INFORMATION: synthetically generated primer

<400> SEQUENCE: 13 tatggc                                                                  6

<210> SEQ ID NO 14
<211> LENGTH: 6
<212> TYPE: DNA
<213> ORGANISM: Artificial Sequence
<220> FEATURE:
<223> OTHER INFORMATION: synthetically generated primer

<400> SEQUENCE: 14 attccc                                                                  6

<210> SEQ ID NO 15
<211> LENGTH: 106
<212> TYPE: PRT
<213> ORGANISM: Artificial Sequence
<220> FEATURE:
<223> OTHER INFORMATION: synthetically generated peptide

<400> SEQUENCE: 15

```
Glu Lys Pro Ala Ala Cys Arg Cys Ser Arg Gln Asp Pro Lys Asn Arg
  1               5                  10                  15
```

```
Val Asn Cys Gly Phe Pro Gly Ile Thr Ser Asp Gln Cys Phe Thr Ser
            20                  25                  30

Gly Cys Cys Phe Asp Ser Gln Val Pro Gly Val Pro Trp Cys Phe Lys
            35                  40                  45

Pro Leu Pro Ala Gln Glu Ser Glu Glu Cys Val Met Gln Val Ser Ala
        50                  55                  60

Arg Lys Asn Cys Gly Tyr Pro Gly Ile Ser Pro Glu Asp Cys Ala Ala
 65             70                  75                      80

Arg Asn Cys Cys Phe Ser Asp Thr Ile Pro Glu Val Pro Trp Cys Phe
                85                  90                  95

Phe Pro Met Ser Val Glu Asp Cys His Tyr
            100             105

<210> SEQ ID NO 16
<211> LENGTH: 57
<212> TYPE: PRT
<213> ORGANISM: Artificial Sequence
<220> FEATURE:
<223> OTHER INFORMATION: synthetically generated peptide

<400> SEQUENCE: 16

Gln Glu Phe Val Gly Leu Ser Pro Ser Gln Cys Met Ala Pro Thr Asn
 1               5                  10                  15

Val Arg Val Asp Cys Asn Tyr Pro Thr Val Thr Ser Glu Gln Cys Asn
            20                  25                  30

Asn Arg Gly Cys Cys Phe Asp Ser Ser Ile Pro Asn Tyr Pro Trp Cys
            35                  40                  45

Phe Lys Pro Leu Gln Glu Cys Thr Phe
     50                  55
```